United States Patent
Nakamura et al.

(10) Patent No.: US 6,821,334 B2
(45) Date of Patent: Nov. 23, 2004

(54) PROCESS FOR PRODUCING SULFONATED SOLID PARTICLES

(75) Inventors: Michiel Nakamura, Tokyo (JP); Yoshiyuki Zama, Tokyo (JP); Hisao Okamoto, Tokyo (JP); Atsushi Nogami, Tokyo (JP); Naoyuki Sakai, Tokyo (JP); Hideyuki Koiso, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 218 days.

(21) Appl. No.: 10/243,660

(22) Filed: Sep. 16, 2002

(65) Prior Publication Data

US 2003/0134938 A1 Jul. 17, 2003

(30) Foreign Application Priority Data

Sep. 19, 2001 (JP) ........................................ 2001-284955

(51) Int. Cl.$^7$ .................... C03C 17/00; C08C 19/20; C09D 5/00

(52) U.S. Cl. .................... 106/473; 106/31.6; 106/31.65; 106/493; 204/471; 205/68; 205/109; 205/118; 252/502; 347/100; 427/212; 427/215; 428/403

(58) Field of Search .............................. 106/31.6, 31.65, 106/473, 493; 204/471; 205/68, 109, 118; 252/502; 347/100; 427/212, 215; 428/403

(56) References Cited

U.S. PATENT DOCUMENTS 5,703,225 A * 12/1997 Shet et al. .................... 536/59
5,849,818 A * 12/1998 Walles et al. .................. 524/8
6,664,340 B1 * 12/2003 Karki et al. ............. 525/333.5

* cited by examiner

*Primary Examiner*—Anthony J. Green
(74) *Attorney, Agent, or Firm*—Oblon, Spivak, McClelland, Maier & Neustadt, P.C.

(57) ABSTRACT

A process produces a sulfonated solid particle by burning sulfur to yield gaseous sulfur dioxide, subjecting the gaseous sulfur dioxide to catalytic oxidation to yield gaseous sulfur trioxide, and sulfonating a dry powdery or granular solid particle with the gaseous sulfur trioxide in a gas phase-solid phase reaction.

20 Claims, No Drawings

PROCESS FOR PRODUCING SULFONATED SOLID PARTICLES

BACKGROUND OF THE INVENTION

1. Field of the Invention

The present invention relates to a process for producing sulfonated solid particles, to such sulfonated solid particles, and to compositions containing the sulfonated solid particles. More specifically, it relates to a process for producing sulfonated solid particles, in which a solid particle is brought into contact with gaseous sulfur trioxide, which gaseous sulfur trioxide is obtained by catalytic oxidation of gaseous sulfur dioxide prepared by burning sulfur. It also relates to sulfonated solid particles obtained by the process, and to use thereof.

2. Description of the Related Art

Conventional water-based coloring agents mainly comprise water-soluble dyes. For example, many of ink-jet inks are water-based inks each containing a water-soluble dye as a coloring agent.

However, such dye-based inks are insufficient in light fastness, water resistance, and other fastness properties. Accordingly, instead of water-soluble dyes, use of pigment-based coloring agents such as inks containing pigments that are excellent in light fastness, water resistance, and other physical properties has been investigated. For example, water-based pigment dispersions are increasingly used in inks for use in wiring materials such as felt tip pens, fiber tip pens, and ball point pens. Ink-jet printers using such pigment-based inks have become commercially practical. In addition, such water-based coloring agents containing almost no organic solvents are increasingly used as coloring agents for use in paints and gravure inks, from the viewpoint of environmental protection.

When pigments are used in water-based inks and other water-based coloring agents, they are finely divided in order to improve sharpness, clearness, and transparency of hue of the pigments. Dispersing agents are required to disperse such finely divided pigments into aqueous media homogeneously and to ensure storage stability of the resulting dispersions. However, such dispersing agents alone cannot ensure long-term stability of the pigment dispersions. As a possible solution to improve the long-term stability of the pigment dispersions, sulfo groups or carboxylic acid groups are introduced into the surfaces of the pigments to modify the same.

In general, organic pigments have weak polarity on their surfaces and thereby have insufficient dispersion stability in disperse media, since their surfaces cannot sufficiently adsorb resin dispersing agents in vehicles by action of, for example, hydrogen bonds. To increase affinity between a pigment and a resin dispersing agent and to thereby improve dispersion stability in dispersing media, the pigment is treated with a pigment derivative comprising a pigment and a group with affinity for a resin dispersing agent in a vehicle or a polar group bonded to the pigment. For example, Japanese Patent No. 1241792 proposes a pigment dispersion comprising a pigment, a resin dispersing agent, and a fluidizing agent having an ammonium sulfonate group.

In coloring agents for use in color filters, it is important to finely divide the pigments in order to improve transparency (clarity), sharpness, transmittance, and other physical properties of the resulting color filters and it is particularly important to ensure fluidity of the pigment dispersions, to avoid aggregation of the pigments and to ensure storage stability of the pigments. To these purposes, such pigment derivatives and pigment dispersing agents are used in the coloring agents for use in color filters.

Under these circumstances, attempts have been made to impart polar groups to the pigments. For example, a process has been proposed, in which the surface of a pigment is sulfonated without the use of conventional materials such as sulfuric acid or fuming sulfuric acid to thereby introduce polar groups to the pigment. In this process, a sulfonating agent that is solid at room temperature (e.g., amidosulfonic acid, sulfur trioxide pyridine complex, and sulfur trioxide dimethylformamide complex) is used in the presence of or in the absence of a solvent. This process requires a pretreatment of finely dividing the pigment before sulfonation, in order to sulfonate the pigment surface homogeneously. When the sulfonation is performed in a solvent, the process further requires, after sulfonation, separation of the sulfonated pigment from the solvent, recovery and purification of the solvent, and neutralization of large amounts of the sulfonating agent as a waste and is economically disadvantageous.

When the pigment is sulfonated by mixing with the sulfonating agent that is solid at room temperature and heating the resulting mixture, conditions for sulfonation such as sulfonation temperature and sulfonation time are difficult to control, since the state of the reaction system varies by whether or not the sulfonation temperature is equal to or higher than the melting point of the sulfonating agent, and the sulfonation temperature should be set at a relatively high temperature (e.g., from about 150° C. to about 210° C.).

Alternatively, carbon powder is sulfonated with gaseous sulfur trioxide obtained by heating and vaporizing solid sulfur trioxide in a laboratory device with a flask. The solid sulfur trioxide used in the process is a highly acidic and highly oxidative compound and is highly toxic to cause inflammation on the mucous membrane and chemical burn on the skin of operators. The solid sulfur trioxide absorbs moisture upon contact with the air and becomes fuming. When it comes into contact with water, it explosively acts upon water and is dissolved therein to yield sulfuric acid. Accordingly, the solid sulfur trioxide in large amounts cannot significantly be used in commercial production from the viewpoints of workability and safety.

SUMMARY OF THE INVENTION

Accordingly, it is an object of the present invention to provide a process for commercially producing sulfonated solid particles in large amounts under mild conditions under which the sulfonation is capable of being easily controlled without the use of solvents. After intensive investigations, the present inventors have found that the object can be achieved by sulfonating a solid particles with gaseous sulfur trioxide obtained by catalytic oxidation of gaseous sulfur dioxide, which gaseous sulfur dioxide is prepared by burning sulfur. The present invention has been accomplished based on these findings.

Specifically, the present invention provides, in an aspect, a process for producing a sulfonated solid particle, including the steps of burning sulfur to yield gaseous sulfur dioxide; subjecting the gaseous sulfur dioxide to catalytic oxidation to yield gaseous sulfur trioxide; and sulfonating a dry powdery or granular solid particle with the gaseous sulfur trioxide in a gas phase-solid phase reaction. In another aspect, the present invention provides a sulfonated solid particle produced by the process, a composition and a coloring composition containing the sulfonated solid particle, as well as use thereof.

The term "solid particle" as used herein means and includes any solid substance that can be sulfonated on its surface, such as organic pigments, carbon black pigments, conductive carbon black, carbon black for use in batteries, carbon black for use in rubber, water-insoluble dyes, and resinous fine particles. Such carbon black substances may be generically referred to as "carbon black fine particles". The solid particle can be of any shape such as powdery, particulate, granular, flaky, and fibril, and these shapes are generically referred to as "powdery or granular" herein.

The process of the present invention can sulfonate solid particles such as organic pigments, carbon black pigments, carbon black and resinous fine particles with the gaseous sulfur trioxide in a gas phase-solid phase reaction and can easily produce sulfonated solid particles with industrial safety at low cost. According to this process, the degree of sulfonation can be freely selected within a broad range. The resulting compositions can be used in known or conventional various applications. In particular, pigment compositions produced according to the process can be used as easily dispersible pigment compositions that are suitable as coloring agents for ink-jet inks and for color filters, as well as coloring agents for regular paints and printing inks. They can also be used as dispersing agents or dispersing assistants for pigments.

DESCRIPTION OF THE PREFERRED EMBODIMENTS

Solid particles to be sulfonated according to the present invention include, but are not limited to, organic pigments, carbon black fine particles, water-insoluble dyes, and resinous fine particles. Such organic pigments include any known organic pigments such as soluble or insoluble azo pigments, polymeric azo pigments, methine-azomethine pigments, azomethine-azo pigments, diketopyrrolopyrrole pigments, phthalocyanine pigments, isoindolinone pigments, isoindoline pigments, anthanthrone pigments, perinone pigments, perylene pigments, anthraquinone pigments, quinophthalone pigments, indigo-thioindigo pigments, dioxazine pigments, quinacridone pigments, and metal complex pigments.

The carbon black fine particles include coloring carbon black pigments, as well as carbon black for use in batteries, conductive carbon black, and carbon black for use in rubber. Such carbon black fine particles include, for example, acetylene black, thermal black, furnace black, lampblack, channel black, and roller black.

The pigments to be sulfonated inclusive of coloring carbon black pigments may have an average particle size equivalent to that in pigments conventionally used in various applications. For example, when the sulfonated pigments are used as coloring agents for regular printing inks and paints, they may have an average particle size the same with commercially available pigments. However, when the sulfonated pigments are used as coloring agents for color filters and as coloring agents for ink-jet inks, their average particle size is preferably from about 0.01 to about 0.5 μm and more preferably from about 0.02 to about 0.2 μm.

According to the process for producing a sulfonated solid particle of the present invention, sulfur is burnt to yield gaseous sulfur dioxide, the gaseous sulfur dioxide is subjected to catalytic oxidation to yield gaseous sulfur trioxide, and the gaseous sulfur trioxide is brought into contact with a dried solid particle such as a pigment in a gas phase-solid phase reaction to directly sulfonate the solid particle. Preferably, the gaseous sulfur trioxide is mixed with a gas inert to the solid particle and gaseous sulfur trioxide before supply to a reaction system containing the dried solid particle. Such inert gas includes, for example, air, nitrogen gas and argon gas. To control the sulfonation easily, it is more preferred to introduce such a gaseous mixture of the inert gas and the gaseous sulfur trioxide into the reaction system than to introduce the gaseous sulfur trioxide alone to the reaction system.

In any embodiment of sulfonation according to the present invention, a sulfonation temperature is preferably from 80° C. to 130° C. and more preferably from 100° C. to 110° C. When the gaseous mixture is used in sulfonation, the concentration of the gaseous sulfur trioxide varies depending on the type and particle size of the pigment to be sulfonated and desired degree of sulfonation but is generally from about 1% to about 20% by mass. The sulfonation time also varies depending on the sulfonation temperature, degree of sulfonation, concentration of the sulfur trioxide in the reaction system, and other parameters but is generally from about 0.5 to about 6 hours, and preferably from about 1 to about 3 hours. However, these sulfonation conditions are not necessarily specified as above, and preliminary investigations thereon may be conducted in some cases.

The degree of sulfonation, i.e., the amount of sulfo groups ($—SO_3H$ groups) introduced into the surface of the solid particle, will be described below. According to the process of the present invention, the gaseous sulfur trioxide obtained in the aforementioned manner is used alone or in combination with an inert gas in sulfonation. This configuration can increase the degree of sulfonation and can achieve a wide variety of degrees of sulfonation by controlling the sulfonation conditions. In particular, the configuration can highly introduce sulfo groups into individual solid particles or individual molecules of the solid particles. In other words, the process of the present invention can achieve a high degree of sulfonation of the solid particles.

When the carbon black fine particles such as carbon black pigments, conductive carbon black, carbon black for use in batteries, and carbon black for use in rubber are sulfonated, sulfo groups are introduced into aromatic nuclei on the surfaces of the individual solid particles. The degree of sulfonation in this case is from about 1% to about 10% by mass, and preferably from about 3% to about 6% by mass per unit mass of the carbon black. When the organic pigments, water-insoluble dyes and resinous fine particles are sulfonated, the sulfo groups are introduced into the surfaces of the individual solid particles or are introduced into inside molecules of the individual solid particles. The degree of sulfonation in these cases varies depending on the type and chemical structure of the pigment in question but is generally from about 0.1% to about 30% by mass, and preferably from about 0.5% to about 10% by mass per unit mass of the pigment.

When the amount of the introduced sulfo groups is excessively small, the resulting sulfonated solid particles such as pigments have insufficient polarity and cannot have satisfactory dispersion stability and storage stability in aqueous or oily media. In contrast, if it is excessively large, the resulting solid particles such as pigments may have decreased fastness properties and other physical properties. A sulfonated pigment with a low degree of sulfonation can be used as a regular pigment. In contrast, a sulfonated pigment carrying at least one sulfo group per pigment molecule (the amount of the sulfo group per unit mass of the pigment is from about 10% to about 30% by mass) can be used as a regular pigment but is preferably used as a "pigment derivative" used in combination with pigments, such as a pigment dispersing agent and dispersing assistant.

The sulfonated pigment obtained according to the process of the present invention is preferably further subjected to neutralization with a basic compound to thereby yield a group of a salt. By this configuration, the sulfonated pigment can more effectively be used in aqueous media and oily media. When the sulfonated pigment is used in an aqueous dispersing media, the sulfo group on the sulfonated pigment can be a free sulfo group or can form a salt with sodium, potassium, calcium, ammonium, an amine or an alkanolamine, for example. When the sulfonated pigment is used in an oily dispersing media, an oligomer or a resin, the sulfo group on the sulfonated pigment can be a free sulfo group, a metal salt, or an organic amine salt as mentioned above. In addition, it can also be a salt of a primary, secondary, or tertiary amine or a quaternary ammonium salt having a hydrocarbon group (e.g., an alkyl group, cycloalkyl group or aryl group) containing 6 or more carbon atoms or a salt obtained by neutralization with a known basic compound such as a polyester oligomer derivative of a polyamine or polyethyleneimine.

Such amines include, but are not limited to, dimethylamine, trimethylamine, diethylamine, triethylamine, n-propylamine, isopropylamine, n-butylamine, t-butylamine, hexylamine, laurylamine, stearylamine, oleylamine, 1,2-dimethylpropylamine, stearylaminopropylamine, and other aliphatic amines; hydroxyethylamine, hydroxypropylamine, N,N-dimethylaminoethanolamine, N,N-diethylaminoethanolamine, N,N-dimethylaminopropanolamine, N,N-diethylaminopropanolamine, and other alkanolamines; cyclohexylamine, pyridine, piperidine, piperazine, morpholine, and other alicyclic amines; aniline, aniline derivatives, and other aromatic amines. Such quaternary ammonium compounds include, for example, methyldistearylammonium compounds, and trimethylstearylammonium compounds.

An aftertreatment of the sulfonated pigment obtained according to the process of the present invention will be described in comparison with a conventional process in which sulfuric acid is used as a sulfonating agent and wasted sulfuric acid is neutralized after sulfonation. For example, when a copper phthalocyanine pigment is sulfonated with sulfuric acid according to the conventional process, sulfuric acid is used in an amount about ten times by mass the pigment. In contrast, for example in Example 1 according to the present invention mentioned below, 100 parts by mass of a granular carbon black pigment was sulfonated with a gaseous mixture of gaseous sulfur trioxide and air and thereby yielded a sulfonated carbon black, the sulfonated carbon black was put into ion-exchanged water, was stirred, and was filtrated. This washing procedure was repeated until pH became constant. A total of 16.9 parts by mass of sodium hydroxide was required to neutralize the filtrates and washings in this process. This corresponds to only 20.7 parts by mass of sulfuric acid used in excess per 100 parts by mass of the pigment. The process of the present invention requires the sulfonating agent (gaseous sulfur trioxide) in a much less amount than the conventional sulfonation process using sulfuric acid and can significantly reduce burdens on liquid-waste treatment and on process steps and costs.

The sulfonated pigment obtained according to the present invention is used as a coloring composition comprising the sulfonated pigment alone and a medium or as a coloring composition comprising the sulfonated pigment, another regular pigment (a pigment not sulfonated) and a medium. In the latter case, the sulfonated pigment serves as a dispersing agent (dispersing assistant) of the regular pigment. In any case, the sulfonated pigment is finely divided and dispersed in an appropriate dispersing medium by an appropriate dispersing means depending on its application. Such dispersing media include, but are not limited to, water, water-hydrophilic organic solvent mixtures, organic solvents, oils and fats, plasticizers, oligomers, and resins. Such dispersing means include, but are not limited to, ball mills, sand mills, attritors, horizontal continuous media mills, vertical continuous media mills, pin mills, triple roll mills, press kneaders, tumbler mixers, Henschel mixers, hammer mills, Banbury mixers, and extruders.

The sulfonated pigments obtained according to the present invention can be used as, for example, coloring agents for paints, printing inks, ink-jet inks, and inks for writing materials; coloring agents for color filters; coloring agents for resins; and dispersing agents (dispersing assistants) for regular pigments (pigments not sulfonated).

Paints in which the sulfonated pigments according to the present invention are used as coloring agents are not specifically limited and include all paints in which known or conventional pigments are used. Such paints (coating materials) include, for example, paints for use in automobiles, paints for use in buildings, paints for use in wood, vehicle and equipment paints, household paints, paints for use in plastics, precoated metal paints, can coatings, marine paints, anticorrosion paints, photo-curable paints, electron beam-curable paints, electrostatic powder coatings, and poly(vinyl chloride) sol paints.

The printing inks are not specifically limited and include all known or conventional printing inks such as letterpress inks, lithographic inks, gravure inks, screen printing inks, news inks, and flexographic inks.

These paints and printing inks may be whichever of solid and liquid. When they are liquid, water, water-hydrophilic organic solvent mixtures, and organic solvents are used as media. Such organic solvents include, but are not limited to, aliphatic hydrocarbons, alicyclic hydrocarbons, aromatic hydrocarbons, halogenated hydrocarbons, esters, ketones, glycol ethers, and alcohols.

Vehicles for use in the paints and printing inks include known or conventional oily or aqueous vehicles depending on their applications. Resins for use as the vehicles include, but are not limited to, alkyd resins, aminoalkyd resins, acrylic resins for baking, acrylic lacquer resins, polyester resins, epoxy resins, butylated melamine resins, methylated melamine resins, rosin-modified phenol resins, polyurethane resins, styrenic resins, styrene/acrylic resins, styrene-diene copolymers, vinyl chloride copolymers, vinyl acetate resins, vinyl acetate copolymers, ethylene-vinyl acetate resins, butyral resins, drying oils, and boiled oils.

The resins to be colored with the sulfonated pigments of the present invention include, but are not limited to, polyethylene resins, polypropylene resins, poly(vinyl chloride) resins, styrenic resins, acrylonitrile-styrene resins, polyester resins, acrylic resins, methacrylic/styrene resins, and acrylonitrile-butadiene-styrene (ABS) resins.

The coloring compositions of the present invention are used as image display materials in a process for displaying images and are used as image recording agents such as ink-jet inks or electrodeposition recording compositions in image recording processes such as ink-jet recording process or electrodeposition recording process.

The ink-jet inks will be illustrated in detail below as a typical example of such coloring compositions. The ink-jet inks comprise coloring agents, water, water-soluble resins as dispersing agents, surfactants, aqueous resin fixing agents (binders), and organic solvents. The ink-jet inks may further comprise additives to further stably be stored and discharged. Such additives include, for example, surface tension regulators, viscosity modifiers, specific resistance regulators, antifoaming agents, and antifungal agents. Water for use in this case should preferably be ion-exchanged water or ion-exchanged distilled water.

The water-soluble resins serving as dispersing agents include, but are not limited to, acrylic resins, acrylic/styrene resins, polyester resins, polyamide resins, and polyurethane resins. Each of these resins can be used alone or in combination. The acrylic resins and acrylic/styrene resins serving as the dispersing agents include, for example, (meth)acrylate-(meth)acrylic acid copolymers, styrene-(meth)acrylate copolymers, styrene-(meth)acrylate-(meth)acrylic acid copolymers, styrene-maleate-maleic acid copolymers, and isobutylene-maleate-maleic acid copolymers. To stably be stored and discharged, the amount of these water-soluble resins serving as the dispersing agents in the ink is generally from about 5% to about 100% by mass, and preferably from about 10% to about 50% by mass based on the mass of the pigment in the ink. The ink may further comprise pH adjusters for these resins, such as inorganic alkaline substances, as well as ammonia, amines, and other organic alkaline substances.

The ink-jet water-based ink may further comprise a surfactant to improve dispersing property and dispersion stability of the pigment and storage stability with time of the ink or to control its surface tension. Such surfactants include, but are not limited to, anionic surfactants such as alkylsulfonates, alkylarylsulfonates, polyoxyethylene alkyl ether sulfonates, and naphthalene sulfonate formaldehyde condensates; nonionic surfactants such as polyoxyethylene alkyl ethers, polyoxyethylene alkyl aryl ethers, polyoxyethylene polyoxypropylene block copolymers, sorbitan fatty acid esters, polyoxyethylene alkylamine ethers, acetylenic alcohols, and acetylenic glycols.

The ink-jet water-based ink further comprises a water-soluble organic solvent in addition to water to prevent the ink and nozzles of a printer head from drying and to improve discharge stability in many cases. Such water-soluble organic solvents include, but are not limited to, polyhydric alcohols such as ethylene glycol, diethylene glycol, polyethylene glycol, and glycerol; polyhydric alcohol ethers such as ethylene glycol monomethyl ether, and ethylene glycol monobutyl ether; alcohols such as methanol, ethanol, and isopropyl alcohol; amines such as diethanolamine, and ethanolamine; heterocyclic compounds such as N-methyl-2-pyrrolidone; and sulfolane.

The coloring composition of the present invention can also be used as a dispersion for color filters. To prepare the dispersion, a dispersing agent and a pigment composition comprising a regular pigment of a desired hue and the sulfonated pigment obtained according to the present invention are added to a solution of an appropriate film-forming resin in an organic solvent, the resulting mixture is premixed to thereby disperse the pigment composition. For example, the pigment composition and the dispersing agent are homogeneously mixed and ground in a dispersing device such as a vertical media mill, a horizontal media mill or a ball mill, and the resulting mixture is added to the solution containing the film-forming resin. Alternatively, the regular pigment and the sulfonated pigment are dissolved in sulfuric acid, the resulting sulfuric acid solution is put into water to deposit a solid solution or eutectoid of the two pigments to thereby yield a pigment composition, and the pigment composition is added to and mixed with a solution comprising the film-forming resin and dispersing agent in the same manner as above, the resulting mixture is milled and thereby yields a pigment dispersion.

Such film-forming resins for use in the present invention are not specifically limited and include known or conventional film-forming resins for use in pigment dispersions for color filters. As the media for use in the pigment dispersion, organic solvents, water, and mixtures of water and organic solvents can be used. The pigment dispersion may further comprise known or conventional additives such as dispersing assistants, lubricating agents, and adhesives.

The amount of the pigment composition in the solution comprising the film-forming resin is preferably from about 5 to about 500 parts by mass per 100 parts by mass of the film-forming resin. The film-forming resin may be whichever of a photosensitive film-forming resin and a non-photosensitive film-forming resin. Examples of solutions containing such photosensitive film-forming resins are those for use in ultraviolet-curable inks and electron beam-curable inks. Examples of solutions containing such non-photosensitive film-forming resins are varnishes for use in printing inks such as letter press inks, lithographic inks, gravure inks, screen printing inks; varnishes for use in air dry or baking paints; varnishes for use in electrodeposition coating; and varnishes for use in thermal transfer printing ribbons.

Such photosensitive film-forming resins include, but are not limited to, photosensitive cyclized rubber resins, photosensitive phenolic resins, photosensitive polyacrylate resins, photosensitive polyamide resins, photosensitive polyimide resins, unsaturated polyester resins, polyester acrylate resins, polyepoxyacrylate resins, polyurethane acrylate resins, polyether acrylate resins, and polyol acrylate resins. In addition, various monomers can be added as reactive diluents.

A photo-curable photosensitive pigment dispersion can be prepared by adding a photopolymerization initiator such as benzoin ether or benzophenone to a pigment dispersion containing a photosensitive resin, and milling the resulting mixture according to a conventional procedure. Likewise, a thermosetting pigment dispersion can be prepared in the same manner as above, except that a thermal polymerization initiator is used instead of the photopolymerization initiator.

The non-photosensitive film-forming resins include, but are not limited to, styrene-(meth)acrylate copolymers, soluble polyamide resins, soluble polyimide resins, soluble polyamide-imide resins, soluble polyester-imide resins, water-soluble salts of styrene-maleate copolymers, water-soluble salts of (meth)acrylate-(meth)acrylic acid copolymers, and water-soluble amino-polyester resins.

Carbon black other than that for coloring can also be sulfonated basically in the same manner as above. In particular, the resulting sulfonated conductive carbon black such as acetylene black is useful for the preparation of water-based dispersions of conductive compositions such as conductive paints or conductive inks. These conductive compositions are used for the production of conductive materials of electronic parts, such as antistatic films and wrapping paper.

As the resinous fine particles, polypropylene and other polyolefin fine particle can be used. However, preferred are particles of styrene-acryonitrile-hydroxyethyl methacrylate-divinylbenzene (mass ratio: 41.6:7.1:8.1:8.7) crosslinked copolymer for use in a charged mosaic membrane disclosed in Japanese Unexamined Patent Application Publication No. 2000-309654, and other particles of styrene-divinylbenzene crosslinked copolymers used as, for example, ion exchange resins.

The process of the present invention has the following features and advantages.

1) The solid particles such as pigments in any shape such as powder, granule, particle, flake, or fibril can be brought into contact with and react with gaseous sulfur trioxide on their surfaces, and the process requires no pretreatment such as fine dispersion of the pigment particles to be sulfonated.

2) Excess gaseous sulfur trioxide after sulfonation can be replaced with an inert gas such as air or nitrogen gas, and sulfur trioxide adsorbed by the sulfonated solid particles can easily be washed and neutralized.

3) The solid particles such as pigments can be sulfonated directly with gaseous sulfur trioxide, and the sulfonation can proceed at low temperatures and can easily be controlled with high efficiency.

4) The solid particles such as pigments are less prone to be damaged in this process.

5) Even pigments and other solid particles susceptible to hydrolysis, such as those which are hydrolyzed by sulfonation with sulfuric acid, can be sulfonated.

6) Excess gaseous sulfur trioxide recovered after sulfonation can be reused in another application.

7) In this process, sulfur is burnt to yield gaseous sulfur dioxide, the gaseous sulfur dioxide is subjected to catalytic oxidation to yield gaseous sulfur trioxide, and the gaseous sulfur trioxide is used as the sulfonating agent. The starting material sulfur is relatively low in hazardous nature. Sulfonation can be controlled only by controlling the flow rate of a gas containing the gaseous sulfur trioxide allover the process steps. The process steps of this process can easily be controlled industrially, and the gaseous sulfur trioxide in large amounts can be treated with less hazard. Accordingly, the process can easily produce sulfonated solid particles with safety.

8) The process does not use organic solvents containing sulfur trioxide complexes as in conventional techniques and can easily treat its wasted liquid and is economically advantageous. The conventional techniques just mentioned above require treatment of large amounts of wasted acids and wasted solvents.

9) Carbon black produced by oxidation of hydrocarbons has few sites to be sulfonated and cannot significantly be sulfonated with sulfo groups according to conventional techniques. However, the process of the present invention allows the gaseous sulfur trioxide to react directly with the target solid particle and can satisfactorily introduce sulfo groups even into such carbon black.

As is described above, the process of the present invention can rationally and easily produce sulfonated solid particles and is economically advantageous.

EXAMPLES

The present invention will be illustrated in further detail with reference to several examples below, which are not intended to limit the scope of the invention. All parts and percentages are by mass unless otherwise specified.

Example 1

A total of 100 parts of a powdery carbon black pigment (average particle size: 0.013 μm) was pre-dried in a dryer at 105° C. for 1 hour and was then placed in a reactor. Separately, sulfur was burnt to yield gaseous sulfur dioxide, and the gaseous sulfur dioxide was subjected to catalytic oxidation and thereby yielded gaseous sulfur trioxide. A mixture of the dry air and the gaseous sulfur trioxide heated at 80° C. to 110° C. was supplied to the reactor with a concentration of the gaseous sulfur trioxide of 8% relative to the dry air, followed by sulfonation for 2 hours. The reaction mixture was cooled, the sulfonated carbon black was put into ion-exchanged water, was stirred and was then filtrated. This washing procedure was repeated until pH became constant. These filtrates were neutralized with 10% sodium hydroxide aqueous solution, which required 16.9 parts of sodium hydroxide in terms of pure substance. This shows that the amount of sulfur trioxide adsorbed by the sulfonated pigment was 20.7 parts in terms of sulfuric acid. Subsequently, the product was dried at 80° C. for 24 hours and thereby yielded 103.4 parts of a carbon black pigment having a sulfonated surface.

The carbon black pigment was decomposed in a combustion flask, and the amount of sulfur in the pigment was determined by ion chromatography to find that the sulfonated carbon black contained 3.2% of sulfo group (—$SO_3H$ group) per its unit mass. Separately, the same carbon black with the above-used one except in the granule form was sulfonated in the same manner as above, and the resulting sulfonated carbon black was found to contain 3.1% of sulfo group (—$SO_3H$ group) per its unit mass.

Example 2

A sulfonated pigment was prepared in the same manner as in Example 1, except that 100 parts of C.I. Pigment Red 122 (hereinafter "C.I." in pigment names will be omitted) (average particle size: 0.1 μm) was used instead of the carbon black pigment. In this procedure, 24 parts of sodium hydroxide was required to neutralize washings after sulfonation. This indicates that the amount of sulfur trioxide adsorbed by the sulfonated pigment was 29.4 parts in terms of sulfuric acid. After drying, 104.5 parts of the sulfonated pigment was obtained. The sulfonated pigment contained 3.9% of sulfo groups per its unit mass, indicating that about 0.15 sulfo group was introduced per molecule of the pigment.

Examples 3 to 13

Sulfonation was performed on yellow pigments, red pigments, blue pigment, violet pigments, and black pigments indicated in Table 1 in the same manner as in Example 1. Table 1 shows the results of sulfonation. On the organic pigments other than carbon black pigment, the numbers of sulfo groups per molecule of the pigments are also shown.

TABLE 1

| Example | Pigment | Average particle size (μm) | Reaction time (hr) | $SO_3H$ per unit mass (%) (number) |
|---|---|---|---|---|
| 3 | Pigment Yellow 147 | 0.35 | 2 | 1.5 (0.11) |
| 4 | Pigment Yellow 173 | 0.72 | 2 | 10.7 (0.58) |
| 5 | Pigment Red 177 | 0.06 | 3 | 4.2 (0.23) |
| 6 | Pigment Red 254 | 0.25 | 2 | 0.7 (0.03) |
| 7 | Pigment Red 255 | 0.35 | 2 | 11.6 (0.42) |
| 8 | Pigment Violet 19 | 0.70 | 2 | 5.3 (0.21) |
| 9 | Pigment Violet 23 | 0.45 | 2 | 14.0 (1.03) |
| 10 | Pigment Blue 15:3 | 0.35 | 2 | 6.2 (0.45) |

TABLE 1-continued

| Example | Pigment | Average particle size (μm) | Reaction time (hr) | SO₃H per unit mass (%) (number) |
|---|---|---|---|---|
| 11 | Aluminum Phthalocyanine Blue | 0.42 | 2 | 4.5 (0.30) |
| 12 | Carbon Black | 0.06 | 3 | 5.4 (—) |
| 13 | CHROMOFINE Black A1103* | 0.30 | 2 | 7.9 (0.77) |

*available from Dainichiseika Color & Chemicals Mfg. Co., Ltd.

Examples 14 to 17

Preparation and Determination of Ink-jet Inks

The sulfonated carbon black pigment obtained in Example 1 was deflocculated in water, was filtrated and thereby yielded a water-based press cake (pigment solid content: 28%). A water-based pigment dispersion was prepared from 17.9 parts of the water-based press cake of the sulfonated carbon black pigment, 3 parts of a water-soluble acrylic resin as a dispersing agent, 14 parts of ethylene glycol, 6 parts of diethylene glycol, 20 parts of glycerol, and 39.1 parts of water. Coarse pigment particles that had not been dispersed were then removed using an ultracentrifuge from the dispersion and thereby yielded an ink-jet water-based black ink having an average particle size of pigment of 72 nm.

Ink-jet water-based yellow, red, and blue inks were prepared in the same manner as above, except that a pigment composition comprising Pigment Yellow 74 and 0.8% of the sulfonated yellow pigment obtained in Example 4 (hereinafter briefly referred to as "PY74-M"), the sulfonated quinacridone red pigment obtained in Example 2, and the sulfonated phthalocyanine blue pigment obtained in Example 10 were used, respectively.

The physical properties of the above-prepared ink-jet water-based inks were determined according to the following methods. The average particle size of a pigment in a sample ink was determined in the following manner. The sample ink was diluted with distilled water to a concentration that is specified by a measuring instrument to yield a test liquid, the test liquid was treated with ultrasound for 20 seconds, and the average particle size of the pigment in the test liquid was determined with a Beckman Coulter N4 Submicron Particle Size Analyzer (available from Beckman Coulter, Inc.). Separately, a sample ink was diluted with water to a pigment concentration of 1% and was subjected to drawdown on a Photo Print Paper No. 2 (available from Seiko Epson Corporation) using a bar coater Specification No. 4 and a K Control Coater (available from RK Print Coat Instrument Ltd.). The color of the test sample was then determined using a differential calorimeter CR-121 (available from Minolta Co., Ltd.). The results are shown in Table 2.

TABLE 2

| | Pigment | Average particle size (nm) | L* | a* | b* | Transparency |
|---|---|---|---|---|---|---|
| Example 14 | Example 1 | 72 | 20.8 | 0.24 | 0.8 | High |
| Example 15 | PY74-M | 115 | 78.4 | −8.7 | 88.2 | High |
| Example 16 | Example 2 | 109 | 51.4 | 62.0 | −5.5 | High |
| Example 17 | Example 10 | 96 | 50.3 | −9.1 | −48.3 | High |

Four-color full-color printing was performed with an on-demand type ink-jet printer containing a piezoelectric vibrator using the above-prepared yellow, blue, red, and black inks and thereby yielded a sharp and clear full-color image.

Example 18

Preparation of Coloring Agent for Color Filters

To an acrylic resin were added Pigment Green 36 (brominated phthalocyanine green) (hereinafter briefly referred to as "PG 36"), the pigment composition according to Example 4 as a dispersing agent, and propylene glycol monomethyl ether acetate (hereinafter briefly referred to as "PGMAc") as a solvent in a proportion indicated in Table 3, the resulting mixture was premixed and thereby yielded a green base color. The acrylic resin used herein had been obtained by polymerizing methacrylic acid, butyl acrylate, styrene, and hydroxyethyl acrylate in a molar ratio of 25:50:15:10 and had a molecular weight of 12000 and a solid content of 30%.

Examples 19 and 20

Blue and red base colors were obtained in the same manner as in Example 18, except that, instead of the brominated phthalocyanine green, Pigment Blue 15:6 (ε type copper phthalocyanine blue) (hereinafter briefly referred to as "PB 15:6") and the red pigment composition according to Example 5 were used, respectively. The formulations of these base colors are shown in Table 3.

TABLE 3

| Formulation (part) | Ex. 18 | Ex. 19 | Ex. 20 |
|---|---|---|---|
| Hue | G | B | R |
| PG 36 | 20 | — | — |
| PB 15:6 | — | 20 | — |
| Pigment of Ex. 5 | — | — | 22 |
| Dispersing pigment composition of Ex. 4 | 2 | — | — |
| agent pigment composition of Ex. 10 | — | 2 | — |
| Acrylic resin | 50 | 50 | 50 |
| PGMAc | 28 | 28 | 28 |
| Total | 100 | 100 | 100 |

Each of the base colors obtained according to Examples 18 to 20 was applied to a glass plate, was dried, and the maximum transmittance and maximum absorption wavelength of the resulting coating were determined. Separately, each of the base colors was stored at room temperature for one month, and a change in viscosity thereof was determined. The results are shown in Table 4.

TABLE 4

|  | Ex. 18 | Ex. 19 | Ex. 20 |
|---|---|---|---|
| Hue | G | B | R |
| Maximum absorption wavelength (nm) | 540 | 455 | 598 |
| Maximum transmittance (%) | 91.5 | 88.0 | 47.2 |
| Viscosity (cP) before storage | 42 | 34 | 39 |
| 1 month later | 58 | 56 | 62 |

Example 21

Preparation and Determination of Paint

To verify the effect of sulfonation surface treatment on a regular non-sulfonated pigment, a paint having the following formulation was prepared.

| | |
|---|---|
| Red pigment composition of Example 6 | 50 parts |
| Xylene | 50 parts |
| Alkyd resin*1 | 100 parts |
| Dispersing agent*2 | 5 parts |

*1: Short-oil alkyd resin with coconut oil (available from Hitachi Chemical Co., Ltd.)
*2: Polyester dispersing agent Solsperse 24000 GR (available from Avecia Ltd.)

The above components were mixed in a high-speed disperser for 30 minutes, and the resulting composition was mixed in a miniature sand mill for 1 hour. To the resulting composition, 367 parts of the alkyd resin (solid content: 50%) and 200 parts of a melamine resin (a butylated melamine resin available from Dainippon Ink and Chemicals, Inc.; solid content: 60%) were further added, the resulting mixture was subjected to kneading finish for 10 minutes and thereby yielded a paint (Primary Color Formulation 1) having a mass ratio in solid contents of the alkyd resin to the melamine resin of 7:3 and a pigment content of 15% relative to the resin solid contents.

The behavior in viscosity of the above-prepared paint (Primary Color Formulation 1) was determined by measuring its viscosity using a B type viscometer at a rotation number of 6 rpm and at a rotation number of 60 rpm. This primary color enamel was applied to a surface coated paper using a 6-mil applicator for drawdown. The resulting drawdown paper was left stand at room temperature for 1 hour and was then left in an oven at 140° C. for 30 minutes to thereby cure the drawdown coating by heat. The gloss of the resulting drawdown article was measured to thereby determine dispersion property of the pigment. The result is shown in Table 5.

Comparative Example 1

A paint was prepared in the same manner as in Example 21, expect that non-sulfonated Pigment Red 254 was used instead of the red pigment composition used in Example 21. The drawdown procedure of Example 21 was repeated using the resulting paint, and the gloss of the drawdown article was measured to thereby determine dispersion property of the pigment. The result is shown in Table 5.

Example 22

Preparation and Determination of Paint

To verify the effect of sulfonation surface treatment on a regular pigment, a paint having the following formulation was prepared.

| | |
|---|---|
| Pigment Red 254 | 47.5 parts |
| Pigment composition of Example 7 | 2.5 parts |
| Mixed thinner*3 | 50.0 parts |
| Acrylic polyol resin*4 | 100.0 parts |

*3: Mixed thinner: a mixture of toluene and butyl acetate in a mass ratio of 6:4
*4: ACRYDIC A-801 available from Dainippon Ink & Chemicals, Inc.

The above components were mixed in a high-speed disperser for 30 minutes, and the mixture was further mixed in a miniature sand mill for 1 hour. To the resulting mixture, 400 parts of the acrylic polyol resin (solid content: 50%) was further added, the resulting mixture was subjected to kneading finish for 10 minutes and thereby yielded a paint (Primary Color Formulation 2) having a pigment content of 20% relative to the acrylic polyol resin solid contents.

A curing agent isocyanate in an equivalent amount was added to the paint enamel (Primary Color Formulation 2), and the resulting mixture was applied to a surface coated paper using a 6-mil applicator for drawdown. The drawdown paper was left stand at room temperature for 24 hours to cure the coating. The gloss of the resulting drawdown article was measured to thereby determine dispersion property of the pigment. The result is shown in Table 5.

Comparative Example 2

A paint was prepared in the same manner as in Example 22, expect that non-sulfonated Pigment Red 254 alone was used instead of the red pigment composition obtained in Example 7. The drawdown procedure of Example 21 was repeated using the resulting paint, and the gloss of the resulting drawdown article was measured to thereby determine dispersion property of the pigment. The result is shown in Table 5.

TABLE 5

|  | Gloss |
|---|---|
| Example 21 | 92.5 |
| Comparative Example 1 | 87.4 |
| Example 22 | 91.7 |
| Comparative Example 2 | 78.8 |

In the above procedure, gloss was determined at an angle of 60° using a digital glossimeter (available from Murakami Color Research Laboratory under the trade name of GM-26D).

Example 23

Preparation of Amine Salt

A total of 100 parts of water-based paste of the phthalocyanine blue pigment composition obtained in Example 10 (pigment content: 25%) was dispersed in water, and a solution of stearylamine in acetic acid and water was added to the dispersion, pH of the resulting mixture was adjusted to about pH 10 with 30% sodium hydroxide aqueous solution and thereby yielded a stearylamine salt of the sulfonated pigment. Thus, 27.3 parts of a phthalocyanine blue pigment composition 2 was obtained.

The following components were homogeneously mixed and dispersed and thereby yielded a blue quick-drying enamel paint which can be quickly dried at room temperature and is for use in metallic materials such as machines and vehicles. The paint was applied to a substrate and was found to form a clear and beautiful coating.

| | |
|---|---|
| Phthalocyanine blue pigment composition 2 | 5.4 parts |
| R titanium white | 2.0 parts |
| Quick-drying styrenated alkyd resin | 72.6 parts |
| Xylene | 6.6 parts |
| Mineral spirit | 13.0 parts |
| 6% Cobalt naphthenate | 0.3 part |
| Anti-skinning agent | 0.1 part |

Example 24

Preparation of Amine Salt

A total of 100 parts of water-based paste of the aluminium phthalocyanine blue pigment composition obtained in Example 11 (pigment content: 32.1%) was dispersed in water, and a solution of stearylamine in acetic acid and water was added to the dispersion, pH of the resulting mixture was adjusted to about pH 10 with 30% sodium hydroxide aqueous solution and thereby yielded a stearylamine salt of the sulfonated pigment. Thus, 32.9 parts of an aluminum phthalocyanine blue pigment composition 3 was obtained.

Preparation of Plastic Molded Article

A total of 5 parts of a finely divided article of the above-prepared aluminium phthalocyanine blue pigment composition 3 was added to 1000 parts of polyethylene, the resulting mixture was injection-molded at 250° C. and thereby yielded a molded article. This molded article had a uniform blue color.

Example 25

Preparation of Anionic Granular Polymer and Charged Mosaic Membrane and Determination of Demineralization Capability

| | |
|---|---|
| Styrene | 41.6 parts |
| Acrylonitrile | 7.1 parts |
| Hydroxyethyl methacrylate | 8.1 parts |
| Divinylbenzene | 8.7 parts |
| Potassium peroxosulfate | 0.5 part |
| Water | 1000 parts |

The above components were placed in a flask, followed by polymerization at 80° C. under flow of nitrogen gas for 8 hours. The resulting polymer had an average particle size of about 180 nm.

The above granular polymer was filtrated, dried and pulverized and thereby yielded a white polymer. A total of 100 parts of the white polymer was pre-dried in a dryer at 105° C. for 1 hour, was placed in a 1-litter flask, and a gaseous mixture of the air and 8% gaseous sulfur trioxide heated at 80° C. to 110° C. was supplied to the flask, followed by a reaction for 3 hours. The treated granular polymer was dispersed in 2 litters of water, was neutralized with sodium carbonate, was filtrated and was washed with water sufficiently. The resulting anionic granular polymer was subjected to analyses by infrared absorption spectrum and ion chromatography and was found to have about one sulfo group per its aromatic ring. The anionic granular polymer was used as an anionic microgel in the subsequent steps.

A cationic microgel was prepared according to the procedure described in Japanese Unexamined Patent Application Publication No. 2000-309654 by allowing a granular crosslinked copolymer of chloromethylstyrene and divinylbenzene (20:1) to react with triethylamine to thereby yield a quaternary ammonium salt.

A coating composition was prepared from 3.0 parts of the cationic microgel, 7.0 parts of the anionic microgel, 10 parts of a hydrogenated product of an acrylonitrile-butadiene resin, and 80 parts of N,N-dimethylformamide. The coating composition was applied to a polypropylene resin coated release paper using a knife coater to form a uniform coating having a dried thickness of about 30 µm. A polypropylene nonwoven fabric was pressed onto the coating, was dried by hot air, was subjected to washing and other aftertreatment and thereby yielded a charged mosaic membrane reinforced by the non-woven fabric substrate.

An aqueous solution of potassium chloride and glucose was subjected to dialysis using a dialysis tank containing deionized water at ambient pressure according to the procedure described in the above publication. As a result, potassium chloride was dialyzed to the dialysate solution but glucose did little, indicating the membrane has satisfactory separation capability.

While the present invention has been described with reference to what are presently considered to be the preferred embodiments, it is to be understood that the invention is not limited to the disclosed embodiments. On the contrary, the invention is intended to cover various modifications and equivalent arrangements included within the sprit and scope of the appended claims. The scope of the following claims is to be accorded the broadest interpretation so as to encompass all such modifications and equivalent structures and functions.

What is claimed is:

1. A process for producing a sulfonated solid particle, comprising the steps of:
   burning sulfur to yield gaseous sulfur dioxide;
   catalytically oxidizing the gaseous sulfur dioxide to yield gaseous sulfur trioxide; and
   sulfonating a dry powdery or granular solid particle with the gaseous sulfur trioxide in a gas phase-solid phase reaction, wherein the solid particle is at least one selected from the group consisting of organic pigments, carbon blacks and water-insoluble dyes.

2. The process according to claim 1, wherein a gaseous mixture of the gaseous sulfur trioxide with a gas inert to the gaseous sulfur trioxide and the solid particle is used in the sulfonating step.

3. The process according to claim 1, wherein the solid particle is one selected from the group consisting of carbon black pigments, conductive carbon black, and carbon black, and wherein the solid particle has a degree of sulfonation of from 1% to 10% by mass, where the degree of sulfonation is defined as the amount of sulfo group —$SO_3H$ per unit mass of the solid particle.

4. The process according to claim 1, wherein the solid particle is one selected from the group consisting of organic pigments and water-insoluble dyes, and wherein the solid particle has a degree of sulfonation of from 0.1% to 30% by mass.

5. The process according to claim 1, additionally comprising the step of:
   neutralizing the sulfonated solid particle with a basic compound.

6. A sulfonated solid particle produced by the process of claim 1.

7. A composition containing a sulfonated solid particle, comprising:
   a medium; and
   the sulfonated solid particle of claim 6 alone or in combination with another solid particle dispersed in the medium.

8. A coloring composition comprising:
   a medium; and
   the sulfonated solid particle of claim 6 dispersed in the medium, the sulfonated solid particle being a sulfonated pigment.

9. A coloring composition comprising:
   a medium;
   a pigment; and
   the sulfonated solid particle of claim 6 as a dispersing agent for the pigment, the sulfonated solid particle being a sulfonated pigment.

10. The coloring composition according to any one of claims 8 and 9, wherein the medium is an aqueous medium, and wherein the coloring composition constitutes a water-based pigment ink.

11. A process comprising recording an image with the coloring composition of any one of claims 8 and 9 as an image recording agent.

12. A process comprising displaying an image with the coloring composition of any one of claims 8 and 9 as an image displaying material.

13. The process according to claim 11, wherein the image recording agent is an ink-jet ink or an electrodeposition recording composition, and wherein the image is recorded by ink-jet recording or electrodeposition recording.

14. An image recording apparatus comprising the coloring composition of any one of claims 8 and 10 as an image recording agent, the image recording agent being an ink-jet ink or an electrodeposition recording composition, and wherein the apparatus serves to record an image by ink-jet recording or electrodeposition recording.

15. An ink-jet printer comprising the coloring composition of any one of claims 8 and 9 as an ink-jet ink.

16. A process comprising recording an image with the coloring composition of claim 10 as an image recording agent.

17. A process comprising displaying an image with the coloring composition of claim 10 as an image displaying material.

18. The process according to claim 16, wherein the image recording agent is an ink-jet ink or an electrodeposition recording composition, and wherein the image is recorded by ink-jet recording or electrodeposition recording.

19. An image recording apparatus comprising the coloring composition of claim 10 as an image recording agent, the image recording agent being an ink-jet ink or an electrodeposition recording composition, and wherein the apparatus serves to record an image by ink-jet recording or electrodeposition recording.

20. An ink-jet printer comprising the coloring composition of claim 10 as an ink-jet ink.

* * * * *

UNITED STATES PATENT AND TRADEMARK OFFICE
CERTIFICATE OF CORRECTION

PATENT NO. : 6,821,334 B2
DATED : November 23, 2004
INVENTOR(S) : Nakamura et al.

It is certified that error appears in the above-identified patent and that said Letters Patent is hereby corrected as shown below:

Title page,
Item [75], Inventors, should read
-- [75]   Inventors:    Michiei Nakamura, Tokyo (JP); Yoshiyuki Zama, Tokyo (JP); Hisao Okamoto, Tokyo (JP); Atsushi Nogami, Tokyo (JP); Naoyuki Sakai, Tokyo (JP); Hideyuki Koiso, Tokyo (JP) --

Signed and Sealed this

Fifteenth Day of February, 2005

JON W. DUDAS
*Director of the United States Patent and Trademark Office*